US011642183B2

(12) United States Patent
Barral et al.

(10) Patent No.: US 11,642,183 B2
(45) Date of Patent: May 9, 2023

(54) SYSTEMS AND METHODS FOR FLEET MANAGEMENT OF ROBOTIC SURGICAL SYSTEMS

(71) Applicant: Verily Life Sciences LLC, South San Francisco, CA (US)

(72) Inventors: Joëlle Barral, Mountain View, CA (US); James Shuma, San Jose, CA (US); Robin Thellend, Sunnyvale, CA (US); Brandon Sprague, Santa Clara, CA (US)

(73) Assignee: VERILY LIFE SCIENCES LLC, South San Francisco, CA (US)

( * ) Notice: Subject to any disclaimer, the term of this patent is extended or adjusted under 35 U.S.C. 154(b) by 877 days.

(21) Appl. No.: 16/429,336

(22) Filed: Jun. 3, 2019

(65) Prior Publication Data

US 2019/0374292 A1 Dec. 12, 2019

Related U.S. Application Data

(60) Provisional application No. 62/681,528, filed on Jun. 6, 2018.

(51) Int. Cl.
*B25J 9/16* (2006.01)
*A61B 34/30* (2016.01)
(Continued)

(52) U.S. Cl.
CPC ............ *A61B 34/30* (2016.02); *A61B 34/25* (2016.02); *B25J 9/1682* (2013.01); *A61B 34/70* (2016.02); *B25J 13/085* (2013.01); *H04L 67/12* (2013.01)

(58) Field of Classification Search
USPC ................................. 700/245–264
See application file for complete search history.

(56) References Cited

U.S. PATENT DOCUMENTS 6,606,744 B1 * 8/2003 Mikurak ............... H04L 9/40
717/174
9,014,848 B2 4/2015 Farlow et al.
(Continued)

FOREIGN PATENT DOCUMENTS

WO 2012109640 8/2012
WO WO-2012109640 A2 * 8/2012 ........... G06F 21/565
WO 2017007795 1/2017

OTHER PUBLICATIONS

Google Cloud , "Google Mobile Management: MDM Solution | G Suite", <https://gsuite.google.com/products/admin/mobile/> downloaded May 2018.
(Continued)

*Primary Examiner* — Jonathan L Sample
(74) *Attorney, Agent, or Firm* — Kilpatrick Townsend & Stockton LLP

(57) ABSTRACT

One method for fleet management of robotic surgical systems includes receiving, by a management server from a robotic surgery system, a provisioning request; in response to receiving the provisioning request: generating an encryption key pair for the robotic surgery system, the encryption key pair comprising a private key and a public key, communicating the private key to the robotic surgery system, and communicating a set of secure certificates to the robotic surgery system, at least one of the secure certificates enabling secure communications between the robotic surgery system and the management server; receiving from the robotic surgery system, and using the at least one secure certificate enabling secure communications, a message indicating one or more software packages, each software package indicating a version of an installed software package on the robotic surgery system; communicating one or more software updates to the robotic surgery system based on the
(Continued)

message; and registering, at the management server, the robotic surgery system.

19 Claims, 9 Drawing Sheets

(51) Int. Cl.
*A61B 34/00* (2016.01)
*H04L 67/12* (2022.01)
*B25J 13/08* (2006.01)

(56) References Cited

U.S. PATENT DOCUMENTS

| | | | |
|---|---|---|---|
| 2007/0022469 A1* | 1/2007 | Cooper | H04L 9/3247 726/3 |
| 2007/0156285 A1 | 7/2007 | Sillman et al. | |
| 2009/0063187 A1* | 3/2009 | Johnson | H04L 67/52 705/2 |
| 2009/0063193 A1* | 3/2009 | Barton | A61B 5/349 340/539.11 |
| 2009/0125337 A1 | 5/2009 | Abri | |
| 2009/0132813 A1* | 5/2009 | Schibuk | G06Q 20/4014 726/9 |
| 2009/0217163 A1* | 8/2009 | Jaroker | G06F 8/60 717/174 |
| 2012/0182939 A1* | 7/2012 | Rajan | A61B 5/002 370/328 |
| 2013/0297973 A1* | 11/2013 | Hyland | G06F 11/3688 714/27 |
| 2013/0346108 A1* | 12/2013 | Kamen | G16H 40/67 705/2 |
| 2015/0207626 A1* | 7/2015 | Neftel | G16H 40/67 713/168 |
| 2015/0223897 A1 | 8/2015 | Kostrzewski et al. | |
| 2016/0036590 A1* | 2/2016 | Barthe | G16H 40/40 713/168 |
| 2016/0129592 A1 | 5/2016 | Saboo et al. | |
| 2017/0220404 A1* | 8/2017 | Polar Seminario | G06F 11/0751 |
| 2017/0228520 A1 | 8/2017 | Kidd et al. | |
| 2018/0004202 A1 | 1/2018 | Onaga et al. | |
| 2018/0122506 A1 | 5/2018 | Grantcharov et al. | |
| 2018/0262388 A1* | 9/2018 | Johnson | H04L 63/0823 |
| 2018/0264347 A1* | 9/2018 | Tran | A63B 43/004 |
| 2018/0317826 A1* | 11/2018 | Muhsin | G06F 13/4004 |
| 2019/0109848 A1* | 4/2019 | Clark | H04L 9/3228 |
| 2019/0349426 A1* | 11/2019 | Smith | H04L 9/0825 |

OTHER PUBLICATIONS

Malhotra, "An Investigation on Cloud Robotics and Automation Control Systems Technology", International Journal of Engineering Innovations & Researc, vol. 4, Issue 3, 2015, 506-509.

Microsoft, "Microsoft Enterprise Mobility + Security—Microsoft 365", <https://www.microsoft.com/en-us/cloud-platform/mobile-device-management> downloaded May 2018.

"Da Vinci Onsite", Intuitive Surgical, Available Online at :https://www.intuitive.eom/-/media/Project/Intuitive-surgical/files/pdf/870312rf-3-17-da-vinci-onsite-sales-siick-427618.pdf?la=en&hash=7ECAD6C7520801B952479AA539004COCAC50E3BB, Mar. 1, 2017, 2 pages.

"OnSite® Overview for the da Vinci Surgical System", Document No. 813331-33 rev E, Available Online at: https://www.davincisurgerycommunity.com/intuitive/docs/813331-33_OnSite_OverView.pdf, Mar. 1, 2017, 13 pages.

Coble et al., "Secure Software Attestation for Military Telesurgical Robot Systems", Military Communications Conference, IEEE, Oct. 31, 2010, pp. 965-970.

Lee et al., "Cyberphysical Systems Security Applied to Telesurgical Robotics", Computer Standards & Interfaces, vol. 34, Issue 1, Jan. 2012, pp. 225-229.

International Application No. PCT/US2019/035450, "International Search Report and Written Opinion", dated Sep. 16, 2019, 16 pages.

* cited by examiner

SYSTEMS AND METHODS FOR FLEET MANAGEMENT OF ROBOTIC SURGICAL SYSTEMS

CROSS-REFERENCE TO RELATED APPLICATIONS

This application claims priority to U.S. Provisional Patent Application No. 62/681,528, titled "Systems and Methods for Fleet Management of Robotic Surgical Systems," filed Jun. 6, 2018, the entirety of which is hereby incorporated by reference.

FIELD

The present application generally relates to robotic surgery systems, and more particularly but not exclusively relates to systems and methods for fleet management of robotic surgical systems.

BACKGROUND

The use of robotic tools to assist with surgical procedures is becoming increasingly common. The robotic tools may assist with any aspect of surgery, including but not limited to insertion or removal of surgical instruments, resection of tissue, insertion of implanted devices, etc. Such robots may be used for a variety of reasons, including because their movements may be more precise and less prone to transient movements. Further, such robots are controlled by one or more persons in an operating room, such as by one or more surgeons. Installation, updating, and servicing of such robotic surgery systems is performed on-site by representatives of the supplier of the robotic surgery system.

SUMMARY

Various examples are described for systems and methods for fleet management of robotic surgical systems. One example method for fleet management of robotic surgical systems includes receiving, by a management server from a robotic surgery system, a provisioning request; in response to receiving the provisioning request: generating an encryption key pair for the robotic surgery system, the encryption key pair comprising a private key and a public key, communicating the private key to the robotic surgery system, and communicating a set of secure certificates to the robotic surgery system, at least one of the secure certificates enabling secure communications between the robotic surgery system and the management server; receiving from the robotic surgery system, and using the at least one secure certificate enabling secure communications, a message indicating one or more software packages, each software package indicating a version of an installed software package on the robotic surgery system; communicating one or more software updates to the robotic surgery system based on the message; and registering, at the management server, the robotic surgery system.

Another example method includes receiving, by a robotic surgery system from a management server, a software update command comprising a signed reference to a new software version; obtaining, by the robotic surgery system, the new software version using the signed reference; validating, by the robotic surgery system, the signed reference to the new software version; receiving, by the robotic surgery system a software installation command from the management server; in response to receiving the software installation command, installing the new software version; and in response to successfully installing the new software version, transmitting a software installation confirmation to the management server.

A further example method includes receiving tracking or diagnostic information from a robotic surgical system; determining a service requirement based on the received tracking or diagnostic information; generating a service request based on the service requirement; and transmitting a message to the robotic surgical system.

One example system for fleet management of robotic surgical systems includes one or more cloud management servers; and a plurality of robotic surgery systems remote from the cloud management server, each robotic surgery system in communication with the cloud management server and associated with a respective medical center, wherein the cloud management server is configured to: receive, from a robotic surgery system located at a medical center, a provisioning request; in response to receipt of the provisioning request: generate an encryption key pair for the robotic surgery system, the encryption key pair comprising a private key and a public key, communicate the private key to the robotic surgery system, and communicate a set of secure certificates to the robotic surgery system, at least one of the secure certificates enabling secure communications between the robotic surgery system and the one or more cloud management servers; receive from the robotic surgery system, and using the at least one secure certificate enabling secure communications, a message indicating one or more software packages, each software package indicating a version of an installed software package on the robotic surgery system; communicate one or more software updates to the robotic surgery system based on the message; and register, at the management server, the robotic surgery system.

One example non-transitory computer-readable medium comprising processor-executable instructions to cause a processor to: receive, from a robotic surgery system, a provisioning request; in response to receipt of the provisioning request: generate an encryption key pair for the robotic surgery system, the encryption key pair comprising a private key and a public key, communicate the private key to the robotic surgery system, and communicate a set of secure certificates to the robotic surgery system, at least one of the secure certificates enabling secure communications between the robotic surgery system and a management server; receive from the robotic surgery system, and using the at least one secure certificate enabling secure communications, a message indicating one or more software packages, each software package indicating a version of an installed software package on the robotic surgery system; communicate one or more software updates to the robotic surgery system based on the message; and register the robotic surgery system.

These illustrative examples are mentioned not to limit or define the scope of this disclosure, but rather to provide examples to aid understanding thereof. Illustrative examples are discussed in the Detailed Description, which provides further description. Advantages offered by various examples may be further understood by examining this specification.

BRIEF DESCRIPTION OF THE DRAWINGS

The accompanying drawings, which are incorporated into and constitute a part of this specification, illustrate one or more certain examples and, together with the description of the example, serve to explain the principles and implementations of the certain examples.

DETAILED DESCRIPTION

Figure 1:
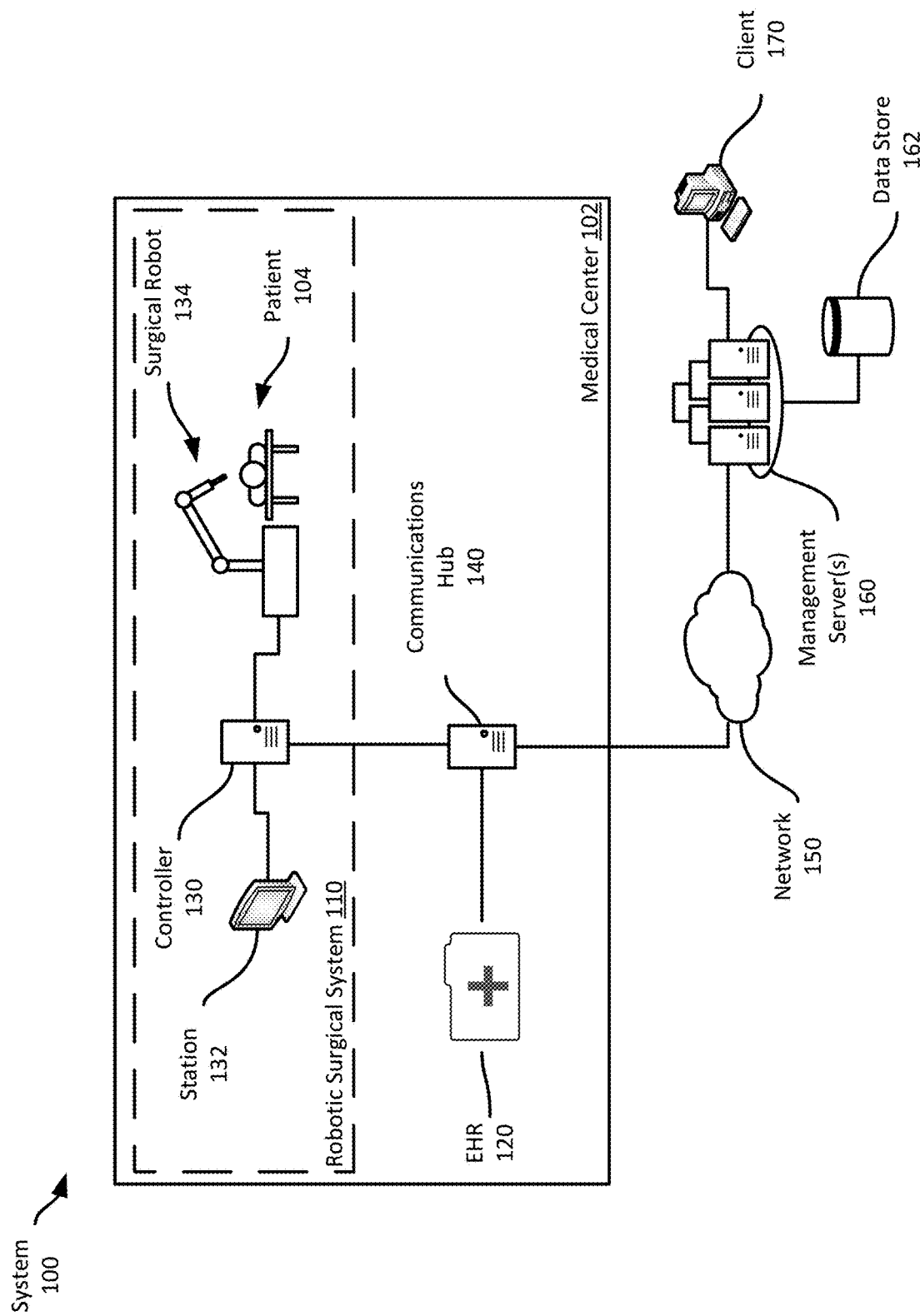
FIGS. 1-3 show example systems for fleet management of robotic surgical systems.

Examples are described herein in the context of systems and methods for fleet management of robotic surgical systems. Those of ordinary skill in the art will realize that the following description is illustrative only and is not intended to be in any way limiting. Reference will now be made in detail to implementations of examples as illustrated in the accompanying drawings. The same reference indicators will be used throughout the drawings and the following description to refer to the same or like items.

In the interest of clarity, not all of the routine features of the examples described herein are shown and described. It will, of course, be appreciated that in the development of any such actual implementation, numerous implementation-specific decisions must be made in order to achieve the developer's specific goals, such as compliance with application and business-related constraints, and that these specific goals will vary from one implementation to another and from one developer to another.

A significant operational difficulty and expense with robotic surgical systems is the amount of support personnel required to install, maintain, troubleshoot, and repair robotic surgical systems at a medical center. Such systems are installed and maintained manually by a representative of the manufacturer or supplier of the robotic surgical system, thus such personnel are virtually always present at medical centers using such robotic surgical systems. This additional personnel creates expense for the medical center or the manufacturer or supplier of the robotic surgical system as it must pay for the support personnel to be present and for work performed on the robotic surgical systems, including provisioning new robotic surgical systems, software updates, diagnostics, etc. Thus, significant cost and efficiency gains may be realized by reducing or eliminating the need for personnel in some or all of these areas.

In an illustrative example of fleet management of robotic surgical systems, a fleet management system is provided at a management facility for a group of medical centers. Each medical center has one or more robotic surgical systems in its operating rooms ("ORs") that may be allocated and used for surgeries. The fleet management system manages each of the robotic surgical systems (or robotic surgical platforms), including monitoring or tracking their usage, monitoring their status or health, detecting faults and failures, installing software updates, scheduling service and maintenance, provisioning new robotic surgical systems, deprovisioning existing robotic surgical systems, etc. Thus, rather than individually managing each robotic surgical system on-site and in-person as discrete systems, this illustrative system enables the centralized provisioning, management, and deprovisioning of robotic surgical systems, which in many cases can reduce or eliminate requirements for on-site personnel and/or make such personnel significantly more productive.

In this example, when a medical center obtains a new robotic surgical system, it may physically setup the components of the robotic surgical system in an OR, and then connect the new robotic surgical system to the medical center's network. Physical setup includes connecting the various components and entering basic information about the fleet management system, such as its network address, into the robotic surgical system. The robotic surgical system can then send a request to the fleet management system to be provisioned and activated, thereby relieving the on-site staff from installing software updates, generating encryption information, and connecting the robotic surgical system to one or more data stores, e.g., patient records, within the medical center.

When the fleet management system receives the provisioning request, it extracts information about the robotic surgical system from the request, including its make and model, or a specific identifier, such as a serial number. The request may also include an identifier of the medical center and information describing its location within the medical center, such as a department or an OR identifier. The fleet management system creates a new record in its data store for the new robotic surgical system. It then creates an encryption public/private key pair for the new robot and transmits the private key immediately to the robotic surgical system. It saves the public key to the newly created record for the robot. The key pair is also assigned an expiration date, which is stored in the newly created record. After sending the private key to the robotic surgical system, the robotic surgical system has been provisioned, but is not yet ready to be activated.

After provisioning the robotic surgical system, the management server then transmits one or more certificates to the robotic surgical system as well as the management server's own public key. The certificates are signed by the management server using its private key, or by another known trusted entity, enabling the robotic surgical system to validate the certificates using the appropriate public key. The certificates can then be used by the robotic surgical system to validate software updates or new software applications, validate surgical tools that may be installed in the surgical robotic system, etc.

In addition to transmitting the certificates to the robotic surgical system, the management server may also request or receive information about software installed on the robotic surgical system, such as the installed software package(s) or the installed version number(s) of such packages. The robotic surgical system responds to the request with a list of installed software packages and version numbers, which the management server inspects to determine whether each installed package is the most current version in use. If any superseded versions of software are identified, the management server transmits one or more messages to the robotic surgical system with the location to obtain each needed software package update. It then awaits confirmation from the robotic surgical system that the identified packages have been installed. Once all packages have been installed, it re-requests information about the software installed on the robotic surgical system. After determining that the updated software has been installed, based on the new list, it marks the robotic surgical system's record as active and makes it available to schedule robotic surgical procedures.

In addition to provisioning and activating a new robotic surgical system, the management server will also request software information from each of the active robotic surgical systems within its data store. In response to determining that any robotic surgical system is not using current software, it will transmit a message to such a system with a location to obtain the latest software update. The robotic surgical system obtains the software update and, upon receipt of a further message to install the software update, it installs the update.

During operation, the robotic surgical system tracks the health of its own components, or the use of detachable or replaceable surgical tools. It can then report such diagnostic information to the management server. The diagnostic information can indicate whether a replaceable tool has reached the end of its usable life, whether one or more components are exhibiting abnormal behavior, or other information that can be analyzed by the management server to identify abnormal behavior or usage trends. Such information can be used by the management server to schedule maintenance or detect errors, failures, or faults. Further, the management server can issue commands to one or more surgical robotic systems to indicate recall items, revoke or recall certificates, prohibit use of such items, or, in an emergency, prohibit operation of the robotic surgical system entirely. Such emergencies may occur upon detection of serious bugs in a software package, withdrawal of regulatory approval for a portion or all of a robotic surgical system, severe operational issues with a particular robotic surgical system, etc.

By centralizing the provisioning, updating, monitoring, and control functionality remotely and autonomously, human intervention in these functions can be significantly reduced. For example, a surgical system may be physically assembled and connected to the hospital's network by hospital staff, at which time, the new robotic surgical system may be autonomously provisioned and updated as described above, and throughout this disclosure. In addition, on-site personnel may no longer be needed to physically inspect or monitor the health of robotic surgical systems. Instead, the management server may be able to autonomously maintain a healthy operational state of one or more robotic surgical systems and only involve personnel when a physical repair or change is needed. Such advantages may significantly reduce the expense in operating and maintaining one or more surgical robotic systems at various locations.

This illustrative example is given to introduce the reader to the general subject matter discussed herein and the disclosure is not limited to this example. The following sections describe various additional non-limiting examples of systems and methods for fleet management of robotic surgical systems.

Referring now to FIG. 1, FIG. 1 shows an example system 100 for fleet management of robotic surgical systems. The example system 100 includes the robotic surgical system 110 located at a medical center 102 that is in communication with one or more remote servers 160 via a communications network 150, e.g., the Internet. The remote management server(s) 160 have an associated data store 162 that may include one or more databases or other servers. A user may use client 170 to access the management server(s) 160, such as to create or edit surgeries to be performed.

The robotic surgical system 110 includes a controller 130, a surgical robot 134, and a station 136 usable by personnel in the OR, such as to view surgery information, video, etc., from the surgical robot 134, which may be used to operate on a patient 104 (though the patient is not part of the robotic surgical system 110). The controller 130 is in communication with an optional communication hub (or "hub," "relay," or "gateway") 140 that can enable, optimize, or improve communication to the remote management server(s) 160 via the network 150. In addition, the communication hub 140 provides access to patient or other medical records stored locally at the medical center 102. Further, in some examples the communication hub 140 may operate as a remote management server 160.

The surgical robot 134 is any suitable robotic system that can be used to perform surgical procedures on a patient 104. A surgical robot 134 may have one or more articulating arms connected to a base, or may lack such articulating arms, depending on its respective configuration. The arms may be manipulated by a controller 130, which may include one or more user interface devices, such as joysticks, knobs, handles, or other rotatable or translatable devices to effect movement of one or more of the articulating arms. The articulating arms may be equipped with one or more surgical instruments to perform aspects of a surgical procedure. Different surgical robots 134 may be configured for particular types of surgeries, such as cardiovascular surgeries, gastrointestinal surgeries, gynecological surgeries, transplant surgeries, neurosurgeries, musculoskeletal surgeries, etc., while some may have multiple different uses. As a result, different types of surgical robots, including those without articulating arms, such as for endoscopy procedures, may be employed according to different examples.

In some examples, surgical robots (or a respective controller, e.g., controller 130) may be configured to record data during a surgical procedure. For example, the surgical robot 134 may record inputs made by the user, actions taken by the surgical robot 134, times (e.g., timestamps) associated with each input or action, video from one or more cameras of the surgical robot, etc. In some examples, surgical robot may include one or more sensors that can provide sensor signals, such as thermocouples, pulse sensors, SvO2 or SpO2 sensors, one or more cameras, etc., or other information to be recorded, such as temperatures, pulse information, images, video, etc. The surgical robot may include its own sensors, which may include accelerometers, position sensors, rotation or translation sensors, force sensors, temperature sensors, electromagnetic sensors, proximity sensors, etc. Such information may be obtained by the sensor and transmitted to a computing device within the surgical robot 134 itself or to the controller 130 for storage. Furthermore, while only one surgical robot 134 is depicted, any suitable number of surgical robots may be employed within a surgical robotic system 100.

The controller 130 in this example includes a computing device in communication with the surgical robot 134 and is able to control access and use of the robot. For example, the controller 130 may require that a user authenticate herself before allowing access to or control of the surgical robot 134. As mentioned above, the controller 130 may include, or have connected to it, one or more user input devices capable of providing input to the controller, such as a keyboard, mouse, or touchscreen, capable of controlling the surgical robot 134, such as one or more joysticks, knobs, handles, dials, pedals, etc.

In this example, the medical center 102 is equipped with a communication hub 140 to help manage several of its robotic surgical systems, including the robotic surgical system 101 shown in FIG. 1. The communication hub 140 is associated with these robotic surgical systems and provides a communication intermediary between the robotic surgical systems and the remote management server(s) 160 as well as access to data within the medical center 102 such as patient records, e.g., EHR 120. The communication hub 140 can also provide some management functionality for the robotic surgical systems. For example, it can proactively obtain software updates from the management server(s) 160 and store them locally at the communication hub 140. When the robotic surgery systems are later instructed to obtain the software updates, the communication hub 140 itself can provide them, rather than requiring the robotic surgical systems to access the management server(s) 160 or another remote computing device.

The communication hub 140 can also store one or more certificates that the robotic surgical systems can use to authenticate communications from the management server(s) 160 or to encrypt data to be sent to the management server(s) 160, whether directly or first stored at the communication hub 140 for later upload. The communication hub 140 can also generate new encryption key pairs for one or more of the robotic surgical systems, such as when an existing key pair has expired or been compromised, store monitoring or diagnostic information, etc. In some examples, the communication hub 140 may intercept messages intended for the management server(s) 160 and respond to the message, such as messages relating to software updates, or anonymize or pseudo-anonymize protected health information ("PHI").

In some examples, the communication hub 140 may also provide other management functionality, such as ensuring at least one robotic surgical system is online and ready at all times. Or it may reschedule or reassign surgeries based on availability of robotic surgical systems or to employ robotic surgical systems that are better suited to a scheduled surgery, such as based on the configurations of the various robotic surgical systems associated with it.

The management server(s) 160 are in communication with one or more data stores 162 and the robotic surgical system 110 via the communication hub 140. In this example, the management server(s) 160 provides a web portal that is accessible by the client 170 via a network connection, such as via the Internet. The web portal provides user access to view or change information about one or more robotic surgical systems, surgeries to be scheduled, medical personnel (e.g., doctors or nurses), etc.

In addition to providing the web portal functionality, the management server(s) 160 provides remote management of one or more robotic surgical systems, sometimes referred to as a "fleet" of robotic surgical systems. In this example, the management server(s) 160 provide remote provisioning and activation of new robotic surgical systems, deprovisioning or removal of robotic surgical systems, software updates to any robotic surgical systems under the control of the management server(s) 160 (referred to as "managed robotic surgical system(s)"), remote usage monitoring, remote health monitoring and error detection in managed robotic surgical systems, emergency remote warnings or shutdown of managed robotic surgical systems, disconnection of managed robotic surgical systems from a communications network, notification of service needs to on-site personnel, user management, mapping of robotic surgical systems to communication hubs, remote teleoperation using managed robotic surgical systems, managing data protections (e.g., based on differing privacy regulations), etc.

While in this example, the management server(s) 160 are shown as being in communication with only a single robotic surgical system 110 and a single communication hub 140, any number of managed robotic surgical systems and communication hubs may be controlled by the management server(s) 160. For example, a network of hospitals or other entity, such as a third party service organization or the robot manufacturer, may manage all robotic surgical systems within each of its various hospitals, surgical clinics, affiliated practices, etc. using a management server (or servers) at a single location. Thus, despite having a potentially large geographic footprint, the network of hospitals may efficiently monitor and maintain its fleet of robotic surgical systems.

Figure 2:
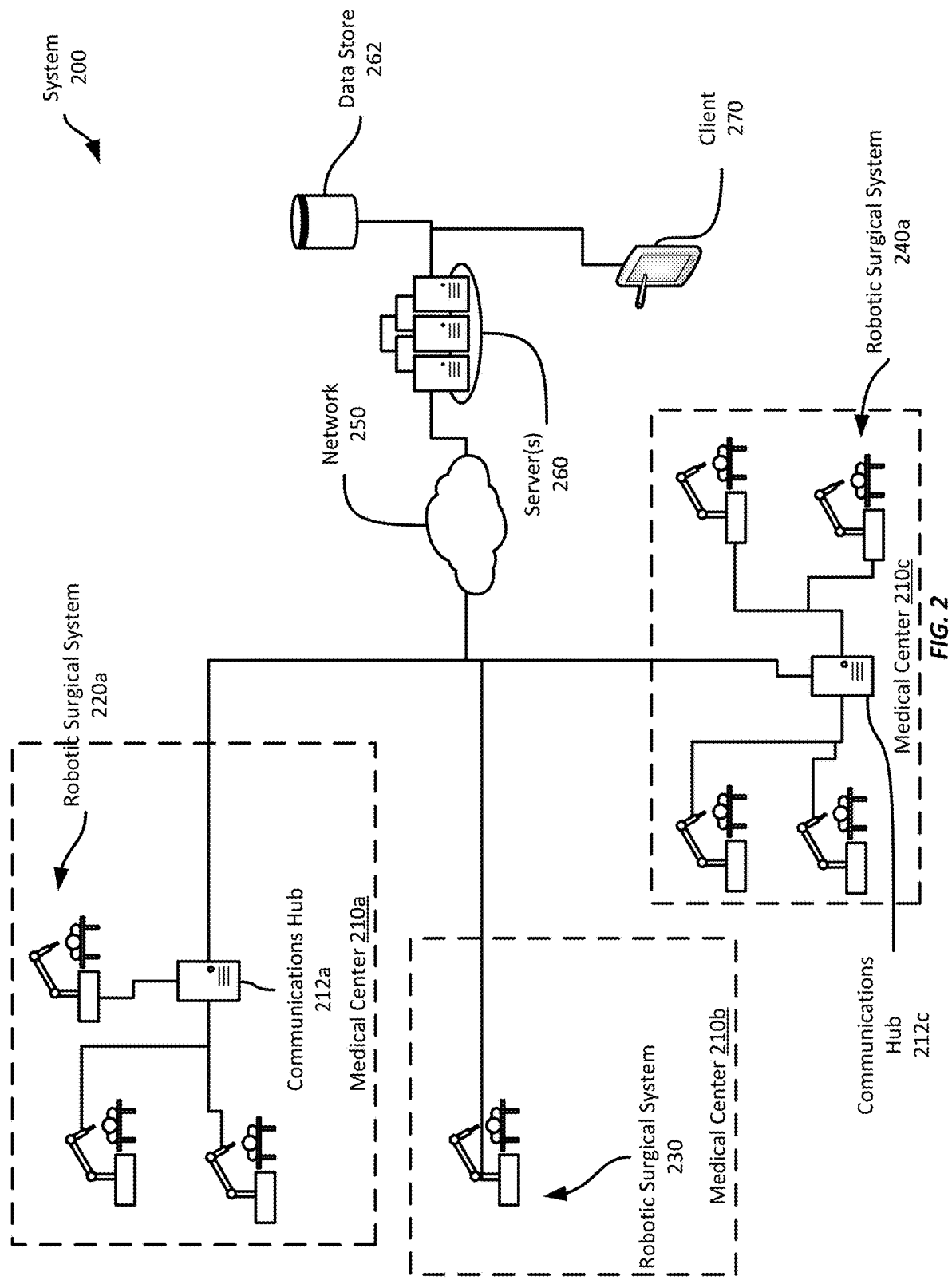

For example, referring now to FIG. 2, FIG. 2 shows another example system 200 for fleet management of robotic surgical systems. In this example, multiple medical centers 210*a-c* within a medical center network (referring to a group of associated medical centers rather than a type of communications network) are all in communication with a common remote management server or group of servers 260. Each medical center 210*a-c* has one or more robotic surgical systems 220*a-c*, 230, 240*a-d* (note that, for space reasons, 220*b-c* and 240*b-d* are shown but not labelled). Each robotic surgical system 220*a-c*, 230, 240*a-d* is in communication with the remote server(s) 260 via a communications network internal to the respective medical center 210*a-c* and then via network 250.

In this example, the robotic surgical systems 220*a-c*, 230, 240*a-d* comprise an example robotic surgical system according to this disclosure, such as the example robotic surgical system 110 shown in FIG. 1. Thus, each includes a surgical robot 134, a controller 130, and a station 132, such as in the examples discussed above with respect to FIG. 1. Further, some medical centers may use one or more communication hubs 212*a*, 212*c*, which may service one or more robotic surgical systems or other equipment at the respective medical center 210*a-c*.

Similar to the example shown in FIG. 1, the management server(s) 260 have an associated data store 262 that may include one or more databases or other servers, and a user may use client 270 to access the management server(s) 260, such as to create or edit new surgeries to be performed substantially as described above with respect to FIG. 1. In addition, the management server(s) 260 provide remote provisioning, activation, management, updating, monitoring and diagnostics, shutdown, etc., as discussed above with respect to FIG. 1. In this example, however, the server(s) 260 manage each of the robotic surgical systems 220*a-c*, 230, 240*a-d*, as well as the two communication hubs 212*a,c*.

Thus, during the course of a day, the server(s) 260 may receive status or diagnostic information from each of the robotic surgical systems 220*a-c*, 230, 240*a-d*, or, at a minimum while connected to a network, a "heartbeat" message indicating that the robotic surgical system is online and is not experiencing any issues. Such a heartbeat message may be transmitted at a certain interval, e.g., every five minutes while the robotic surgical system is online. It should be appreciated that each robotic surgical system 220*a-c*, 230, 240*a-d* may not be powered on or connected to a network at all times. For example, to reduce power consumption or for other reasons, a medical center may power off or disconnect from its network one or more of its robotic surgical systems, such as if it has no surgeries scheduled for a particular day, or for a minimum threshold period of time. Then, prior to a scheduled surgery, e.g., an hour prior, a member of a surgical team or a surgical department may power on or connect the robotic surgical system. However, such operations may disrupt the management features of the management server(s). For example, if software updates are needed for a robotic surgical system that is powered off, the management server may not be able to notify the robotic surgical system to obtain the software update. Thus, in some examples, the management server(s) 260 may opportunistically obtain operational data from robotic surgical systems, e.g., when it first detects they are powered on or connected to a network, or may transmit one or more messages to a communication hub associated with the robotic surgical system to delegate responsibility to obtain information from the robotic surgical system, apply updates, etc. when the communication hub detects the robotic surgical system is online.

Thus, in some examples, communication hubs, e.g., communication hubs 212a,c, may provide some management of managed robotic surgical systems as delegates of the management server(s) 260. For example, a communication hub 212 a,c may obtain copies of software update packages based on one or more messages received from the management server 260 indicating one or more software updates being needed. The communication hub 212 a,c may also maintain records of installed software packages on each robotic surgical system associated with the communication hub. Thus, the communication hub 212 a,c may intercept a message to the robotic surgical systems requesting software version information, and may then respond on their behalf. Such an architecture may enable accurate software versioning, even when one or more robotic surgical systems is offline.

In addition to, or instead of, software version information, the communication hubs 212a,c may also maintain configuration of each associated robotic surgical system. Configuration information may indicate which surgical tools are attached to a particular robotic surgical system, how many controllers or stations are included in the robotic surgical system, a date or time of a last service or maintenance event, components that were serviced or replaced at the last service or maintenance event, etc. Such information may be provided by the respective robotic surgical system itself, or by some or all of its subcomponents, e.g., by the controller, the station, one or more surgical tools, etc. Further, some such information may be manually entered. In some examples, the communication hub 212a,c may also maintain or cache performance, monitoring, or tracking information provided by one or more robotic surgical systems. Such information may include information recorded during a surgery, such as video, sensor information, notes, comments, or other information obtained during the course of a surgery. It may include information from monitoring systems within the robotic surgical system, such as information about actuators, surgical tools, sensors, or other electronic or mechanical components of the robotic surgical system. The robotic surgical system may obtain and store such information during a surgery and, following the surgery, upload the information to the communication hub, or it may stream some or all of such information during the surgery, such as in real-time, with a delay, in segments, etc., to the communication hub, where it is stored for immediate or later upload to the management server or to another remote computing device or storage location. Thus, the communication hubs 212 a,c may provide remote fleet management functionality delegated to it by a management server, or it may provide an intermediate repository for information about one or more robotic surgical systems associated with it.

It should be appreciated that a medical center may employ multiple communication hubs. Such hubs may be assigned to different sets of robotic surgical systems, or may be assigned as primary or backup hubs for different robotic surgical systems. In some examples, different communication hubs may be assigned different roles. For example, one communication hub may be dedicated to obtaining software updates for the robotic surgical systems and diagnostic information from the robotic surgical systems, while another hub may be dedicated to receiving information obtained during surgical procedures and uploading such information to the remote server(s) 260.

In some examples, however, one or more of the managed devices may remain disconnected from a network at all times. In such an example, the remote server(s) 260 may still manage such devices; however, it lacks direct control over them. Instead, the remote server(s) 260 may communicate with a medical center and request information about its robotic surgery systems, communication hubs, etc., which may then be obtained manually, such as by a technician entering such information manually, e.g., via keyboard or touchscreen, or by manually obtaining one or more electronic files from the devices. The remote server(s) 260 may use such information as discussed herein; however, software updates, service requests, shutdowns, etc. may be instead routed to a technician who then manually performs the identified management function, such as obtaining and installing software updates, performing service or maintenance on the device(s), etc.

Figure 3:
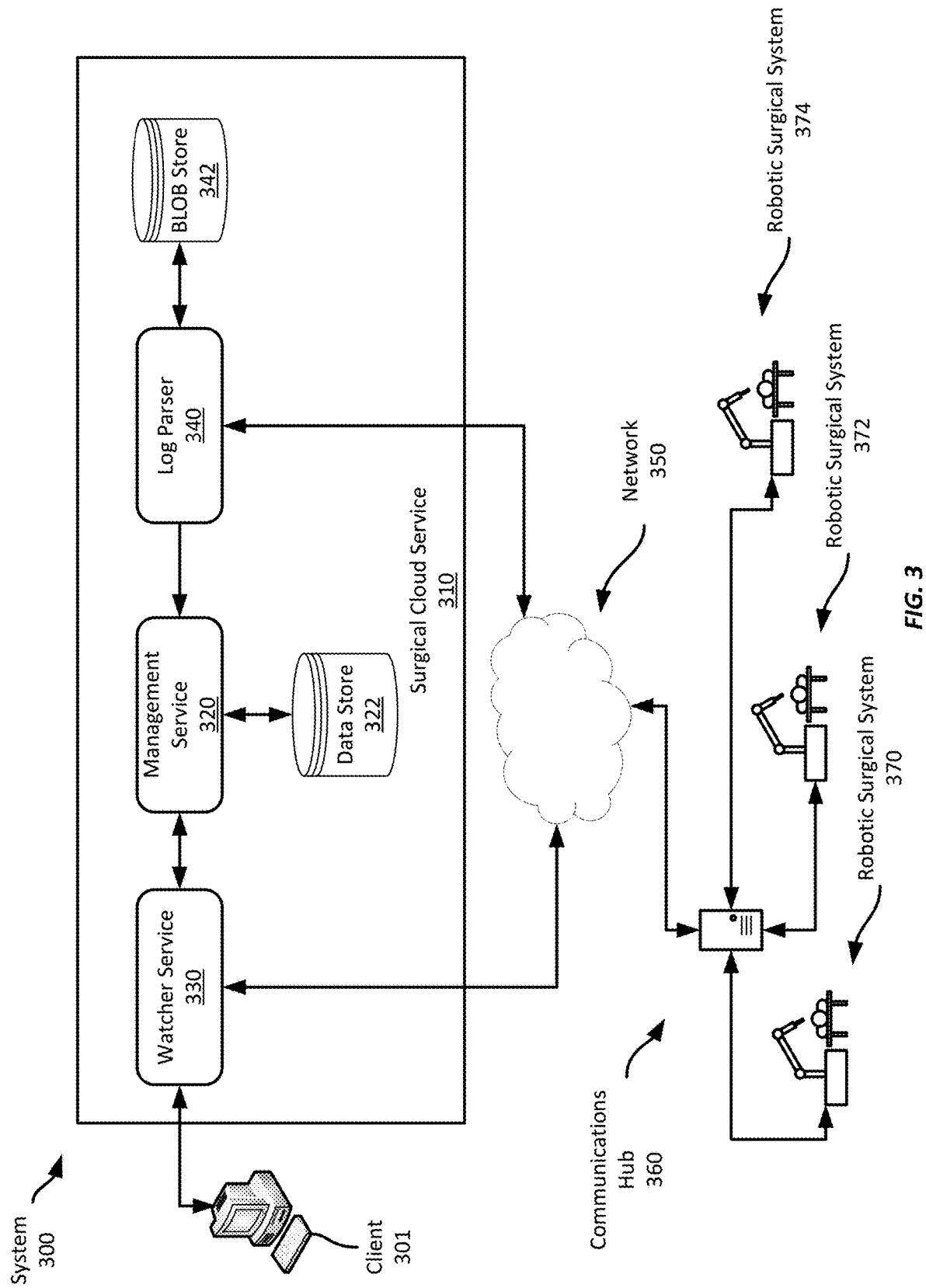

Referring now to FIG. 3, FIG. 3 shows an example system 300 for fleet management of robotic surgical systems. This example system includes a surgical cloud service 310 that is in communication with several robotic surgical systems 370-374 via a network 350. Further, communications between the surgical cloud service 310 and robotic surgical system 370 is facilitated by communication hub 360. The robotic surgical systems 370-374 are any suitable robotic surgical systems, such as those discussed within this detailed description. The communication hub 360 is a suitable communication hub according to this disclosure.

In this example, the surgical cloud service 310 provides functionality available to the robotic surgical systems 370-374, which includes a management server 320, a watcher service 330, and a log parser 340, as well as two data stores 322, 342.

In this example, the management service 320 provides management functionality such as described above with respect to FIGS. 1-2, including remote provisioning, activation, management, updating, monitoring and diagnostics, shutdown, etc. The management service 320 may interact with the watcher service or the log parser to send messages to the various managed devices 360, 370-374 or to receive information from those devices 360, 370-374.

In some examples, the management service 320 may help prepare new software updates for release to the managed devices 360, 370-374. For example, the management service 320 may be provided with a new software package, such as via a web portal. The management service 320 may then generate a check value, such as a hash value (e.g., MD5 hash), for the software update and use the check value to generate a signed universal resource locator ("URL") for the software update, and then upload the software package to the generated URL. After uploading the software package, the management service 320 may then verify the upload, such as by downloading the software package and comparing the calculated check value for the downloaded version with the originally generated check value. After doing so, the management service 320 may confirm to the web portal that the update is ready to be deployed, and may initiate updating one or more managed devices 360, 370-374.

The data store 322 stores information about each device managed by the management service 320, including each of the robotic surgical systems 370-374 and the communication hub 360. For example, the data store 322 may include one or more records for each managed robotic surgical system 370-374, such records may include an identifier for the robotic surgical systems, the different installed components or surgical tools in each robotic surgical system, the versions of such components or surgical tools, usage information for the robotic surgical systems or their respective components or surgical tools, service or maintenance records or status, monitoring or diagnostic information received from the robotic surgical system or the log parser 340, operational status (e.g., provisioned, active/inactive, online, in-use, offline, standby, one or more error conditions, emergency shutdown, etc.), encryption key information (e.g., the respective robotic surgical system's public key), etc.

The watcher service 330 in this example provides a web portal interface between a client device 301 and the management service 320, such as to enable a user to view or edit information related to one or more robotic surgical systems 370-374, or to obtain information from the binary large object ("BLOB") store, such as video or logged information for a surgical procedure. It also provides access to the network 350 for the management service 320. Thus, if the management service 320 determines a command to send to a robotic surgical system, it may transmit the command to the watcher service, which may then package the command into a form suitable for communication across the network 350. In some examples, however, the watcher service 330 may work with the management service 320 to perform one or more management functions.

In one example, the watcher service 330 may receive periodic status messages, such as "heartbeat" messages, from the managed device 360, 370-374, and communicate changes in operational status to the management service 320, which can update one or more records stored in the data store 322. In addition, the watcher service 330 may obtain other information from the managed device 360, 370-374, such as software version information, changes in surgical tools connected to a robotic surgical system, surgeries in-progress, scheduled service or maintenance, error, failure, or fault conditions, etc. The watcher service 330 may then provide such information to the management service 320 or may disregard such messages, if no change in state has occurred. Thus, the watcher service 330 may work with the management service 320 to provide management functionality discussed above.

The log parser 340 may receive information from one or more robotic surgical systems 370-374 and either provide it to the management service 320 or store it in the BLOB store 342. For example, the log parser 340 may receive video, audio, or other data captured during a surgical procedure and store it in the BLOB store associated with a record for the surgery, such as by associating it with a surgical case code, a patient identifier, a surgeon, etc. The log parser 340 may also receive information from one or more of the managed device 360, 370-374 indicating faults, failures, errors, or other operational information, such as use of particular tools, or other diagnostic information logged by the respective managed device 360, 370-374. Such information may be parsed by the log parser 340 to extract the different types of information, which may then be forwarded to the management service 320, which may use the information to detect anomalies, trends, expiration or end-of-life for a surgical tool or component, etc. Such information may be stored in the data store 322 in one or more records associated with the respective managed device 360, 370-374.

It should be appreciated that while this example system 300 includes several discrete software components, no such architectural limitation should be inferred. Rather, any or all of the components shown in the surgical cloud service 310 may be integrated together or separately implemented as two or more discrete software components. Further such discrete software components may execute on discrete computing devices in communication with each other via one or more networks.

Figure 4:
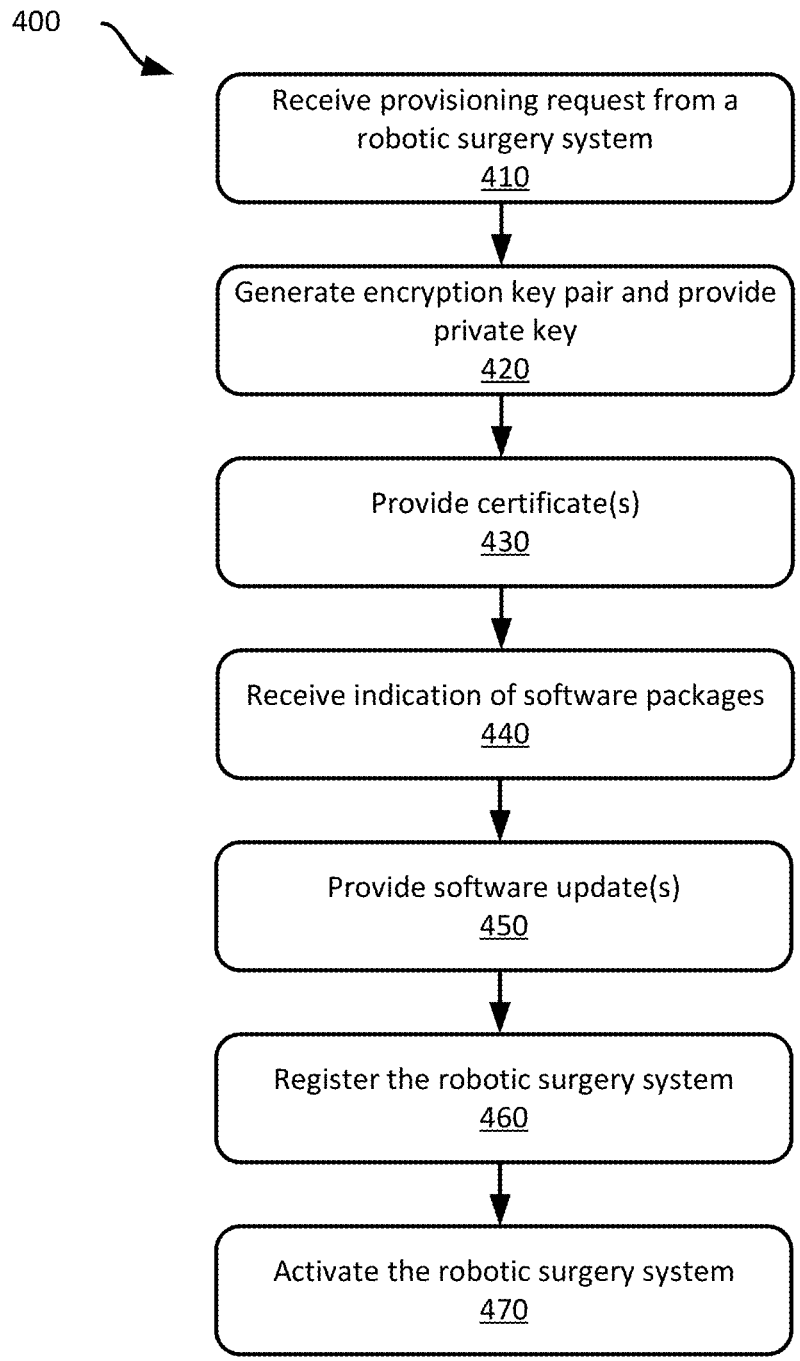
FIGS. 4 and 6-8 show example methods for fleet management of robotic surgical systems.

Referring now to FIG. 4, FIG. 4 shows an example method 400 for fleet management of robotic surgical systems. This example will be discussed with respect to the example system 300 shown in FIG. 3; however, any suitable system according to this disclosure may be employed, including those shown in FIGS. 1 and 2.

At block 410, the management service receives a provisioning request from a robotic surgical system 370. In this example, the robotic surgical system 370 is assembled at a medical center, connected to the medical center's internal network, and powered on. It is then configured with the network addresses for the communication hub 360 and the surgical cloud service 310. After receiving the configuration information, it generates and transmits a provisioning request to the surgical cloud service 310 via the communication hub 360. In this example, the provisioning request includes an identifier for the robotic surgical system, its network address, the network address for its communication hub, an identifier for the medical center, configuration information (e.g., installed components or surgical tools), software version information, etc. The communication hub receives the provisioning request and creates a new local record for the new robotic surgical device 370, and forwards the provisioning request to the surgical cloud service 310.

In some examples, the robotic surgical device 370 may send the provisioning request to the communication hub 360 rather than the surgical cloud service 310. In one such example, the communication hub 360 receives the provisioning request and creates a local record for the robotic surgical device using information within the request, such as described above. The communication hub 360 then transmits a provisioning request to the surgical cloud service 310 to provision the robotic surgical device 370. The provisioning request transmitted by the hub 360 may be the same as the provisioning request received by the hub 360, or it may have a different format or include different or additional information, such as the hub's identifier, etc.

In some examples, the communication hub 360 may intercept a provisioning request sent by the robotic surgical device 370 directed to the surgical cloud device 310 and, rather than forwarding the request, may instead generate a new provisioning request for the robotic surgical device 370, which may include information received from the robotic surgical device 370 and other information, such as the hub's identifier, information about the medical center, etc. Such an example may be employed if specific provisioning information for the medical center or the communication hub is employed. In such an example, the robotic surgical device 370 may not detect that it is communicating with a communication hub 360, but instead may communicate with the communication hub 360 as though the communication hub 360 were the surgical cloud service 310.

After receiving the provisioning request, the surgical cloud service 310 creates a new record in the data store 320 based on the provisioning request.

At block 420, the surgical cloud service 310 generates an encryption key pair and provides one of the keys to the robotic surgical system 370. Any suitable encryption key pair generation technique may be employed, such as an RSA asymmetric encryption key technique, an elliptic-curve cryptographic technique, or any other suitable technique to generate a key pair to enable secure communications, entity verification, or data authentication. The key pair in this example includes a public key and a private key. The surgical cloud service 310 stores the public key in the newly created record in the data store, transmits the private key to the robotic surgical device 370, and upon receiving confirmation that the private key has been successfully received, the surgical cloud service 310 can then delete the private key from its memory.

At block 430, the surgical cloud service 310 provides one or more certificates to the robotic surgical system 370. In this example, the surgical cloud service 310 provides a certificate signed by the surgical cloud service's own private key and a copy of the surgical cloud's public key. The surgical cloud service 310 may also provide one or more certificates associated with providers of software for the robotic surgical system, one or more certificates associated with the communication hub 360, etc., as well as corresponding public keys for entities associated with the certificates. Such certificates may enable the robotic surgical system 370 to validate communications or software received from such entities, enable encrypted communications with the surgical cloud service 310, the communication hub 360, or other suitable entity.

In some examples, the surgical cloud service 310 may have already provided one or more certificates to the communication hub 360. Thus, rather than re-transmit the certificates, the surgical cloud service 310 may instead transmit a message to the communication hub 360 indicating that the robotic surgical system 370 is provisioned and that the communication hub 360 should transmit certificates to the robotic surgical system 370. In response to receiving such a message, the hub 360 may provide copies of one or more certificates to the robotic surgical system 370. Further, in some examples, copies of the certificates may be provided to the communication hub 360, but not to the robotic surgical system 370 itself. Instead, decryption or authentication of software packages or other information may be performed by the communication hub 360 which may then provide the software packages or information to the robotic surgical system 370, if properly validated or decrypted.

At block 440, the surgical cloud service 310 receives a message indicating one or more software packages installed on the managed device, each software package indicating a version of an installed software package on the robotic surgical system. In this example, the robotic surgical system 370 transmits a message to the surgical cloud service 310 identifying its installed software packages and the version number of each. In some examples, such information was supplied within the provisioning request message at block 410, thus block 440 may be omitted in such examples.

At block 450, the surgical cloud service 310 checks the software packages and versions installed on the robotic surgical system 370 to determine if newer versions of any such software packages are available, or if any software package(s) have not been installed on the robotic surgical system 370. If one or more software updates is needed, the surgical cloud service 310 provides the software packages to the robotic surgical system 370. In this example, the surgical cloud service 310 provides a URL for each software package to be updated or installed on the robotic surgical system 370. In some examples, the surgical cloud service 310 may provide only one URL that provides an entirely new set of software to the robotic surgical system 370. For example, the surgical cloud service 310 may entirely replace all software installed on the robotic surgical system 370 with an entirely new software package.

In other examples, the surgical cloud service 310 may transmit a message to the communication hub 360 to instruct it to push one or more software packages to the robotic surgical system 370 and to instruct the robotic surgical system 370 to install such packages. Similarly, the surgical cloud service 310 itself may push one or more software packages to the robotic surgical system 370 to be installed. Still other examples may employ any other suitable technique to provide one or more software updates to the robotic surgical system 370.

At block 460, the surgical cloud service 310 registers the robotic surgical system 370 as being provisioned. In this example, the registering occurs after the robotic surgical system 370 has received its private encryption key, the certificate(s), and software updates; however, in some examples, the surgical cloud service 310 may register the robotic surgical device 370 as provisioned after successfully generating the key pair and providing the private key to the robotic surgical system 370. In this example, the surgical cloud service 310 registers the robotic surgical system 370 by creating a new record in the data store 320 and updating the newly created record to indicate that the robotic surgical system 370 is provisioned but not activated. In this example, when provisioned but not activated, the robotic surgical system 370 may be accessed remotely via the web portal from the surgical cloud service 310, but may not be scheduled for any surgical procedures.

At block 470, the surgical cloud service 310 activates the robotic surgical system 370. In this example, the surgical cloud service 310 awaits confirmation from the robotic surgical system 370 that the software updates were successfully applied before activating the robotic surgical system 370. In response to receiving such confirmation, the surgical cloud service 310 updates the data store record for the robotic surgical system 370 to indicate that it is provisioned and activated. Once the robotic surgical system 370 has been activated, it is available to be used for surgical procedures. Thus, in some examples, it may be tied to a care management platform to plan or schedule surgeries, or it may operate in a standalone mode where it may be used at any time it is idle.

It should be appreciated that the blocks of this example method 400 were presented in a particular order; however, any suitable ordering may be employed according to different examples. For example, blocks 420 and 430 may be combined or performed in a different order. Further, as discussed above, block 460 may be performed between blocks 420 and 430. Further, the use of a robotic surgical system is not precluded if method 400 is not performed. Rather, the robotic surgical system may be used as-is once assembled and powered on; however, its functionality may be reduced until it is registered and activated with a surgical cloud service 310. For example, the robotic surgical system may be used to perform a surgery, but not be allowed access to PHI, or to upload data to the surgical cloud service, etc., until such time as it has been registered and activated.

While the example method 400 was described with respect to provisioning a robotic surgical system, such a method may also be used to provision and activate any managed device 360, 370-374, such as a communication hub 360. For example, a new communication hub 360 may transmit a provisioning request to the surgical cloud service 310, at which time, an example method may proceed to block 410 to provision and activate the communication hub 360.

Figure 5:
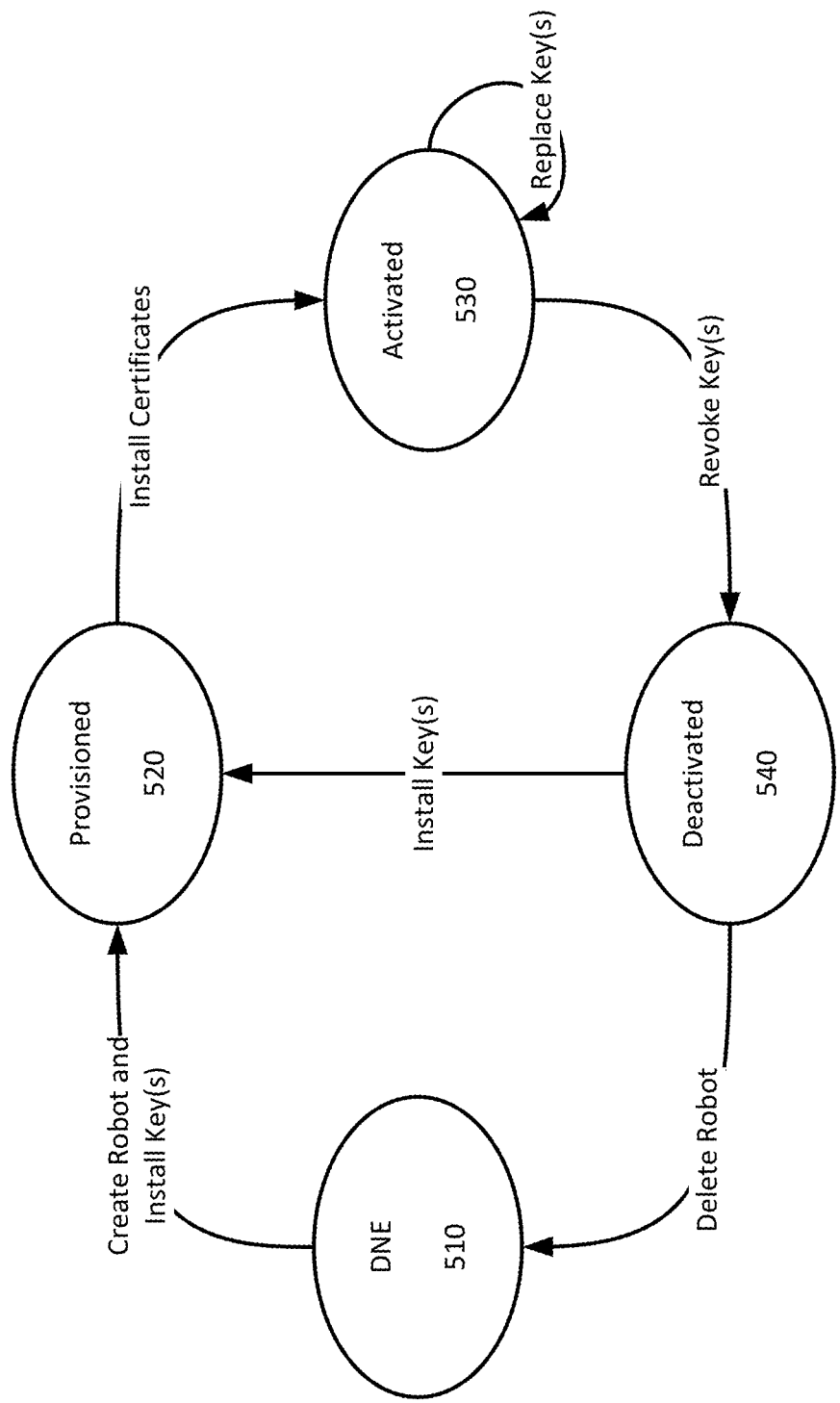
FIG. 5 shows an example state diagram for provisioning and activating a robotic surgical system.

Referring now to FIG. 5, FIG. 5 illustrates different activation states that may be employed in one example system according to this disclosure. As discussed with respect to FIG. 4, the method 400 provisions and then activates a new robotic surgical system 370. With reference to both FIGS. 3-5, at block 410, the robotic surgical system 370 is in state 510: does not exist ("DNE"). Thus, the robotic surgical system 370 does not exist within the surgical cloud service's data store 310. However, once the robotic surgical system 370 is provisioned, but not activated, it transitions to state 520 "Provisioned." As discussed above, when a robotic surgical system 370 is at state 520, it is known to the surgical cloud service 310, but is not available to be scheduled or used for any surgical procedure.

However, once it has been activated as discussed above with respect to FIG. 4, it transitions to state 530, where it is Activated. At this state, it may be scheduled and used for surgical procedures. In some examples, the robotic surgical system 370 may be assigned a new private key, e.g., the original key pair may expire after a predetermined period of time. However, replacing a key pair does not require re-provisioning the robotic surgical system 370 in this example, and it remains at the Activated state 530; though in some examples, re-provisioning may be desirable.

At some time, a robotic surgical system 370 may need to be deactivated, such as if it is to be replaced, moved to a new medical center, or serviced for an extended period of time, or otherwise re-provisioned. Thus, the surgical cloud service 310 may revoke the robotic surgical system's private key, transitioning it to the Deactivated state 540. At state 540, the robotic surgical system 370 may be re-provisioned by providing a new private key, such as by re-performing the method 400 of FIG. 4. However, in some examples, the robotic surgical system 370 may be entirely removed from the surgical cloud service 310 and its record deleted from the data store 320. Such an action returns the robotic surgical device to the DNE state 510, where it is unknown to the surgical cloud service 310. Thus, the surgical cloud service 310 may efficiently provision, activate, deactivate, and delete one or more robotic surgical systems using such techniques according to this disclosure.

Figure 6:
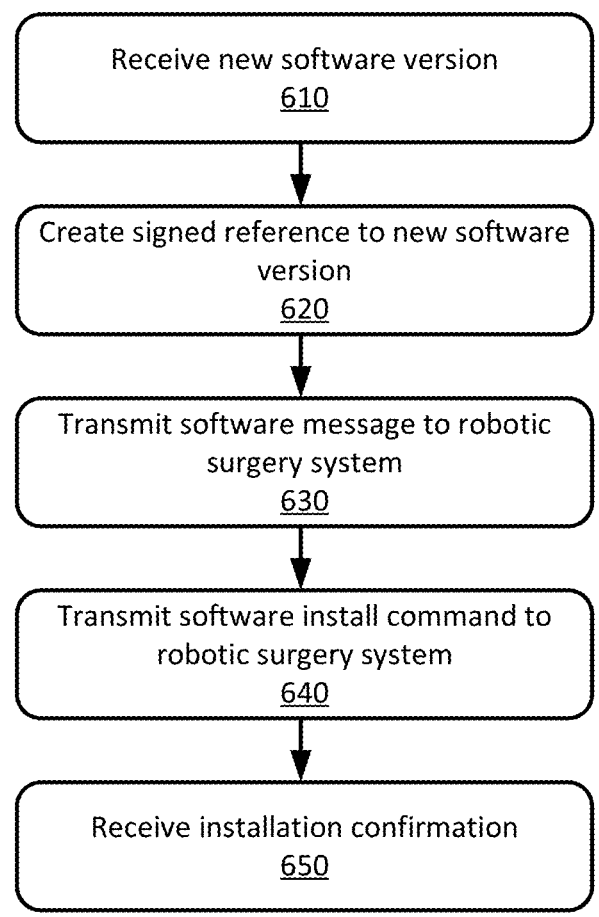

Referring now to FIG. 6, FIG. 6 shows an example method 600 for fleet management of robotic surgical systems. This example will be discussed with respect to the example system 300 shown in FIG. 3; however, any suitable system according to this disclosure may be employed, including those shown in FIGS. 1 and 2.

At block 610, the surgical cloud service 310 receives a new version of software usable by one or more managed device 360, 370-374. For example, a user of a web portal provided by the surgical cloud service 310, e.g., an administrator, may upload a software package update to the surgical cloud service 310, such as by interfacing with the management service 320 via the watcher service 330. In some examples, the user may also provide verification information, such as a check value, e.g., an MD5 hash.

At block 620, the management service 320 generates a signed reference for the received software package update, and if provided, verifies the received software package against the check value. If a check value is not provided, the management service 320 may create a check value. In this example, the management service 320 generates the signed reference by encrypting the check value using its private key. The management service 320 then generates a URL using the signed reference, such as by creating a new directory within the surgical cloud service's domain corresponding to the generated URL, and copies the received software package update to the new directory.

At block 630, the surgical cloud service 310, e.g., via the management service 320, generates and transmits a message, including the generated URL, to one or more managed device 360, 370-374 indicating the new software update is available and should be obtained. In response, the managed device(s) 360, 370-374 employ the URL to obtain the software update. In some examples, a communication hub 360 may intercept the message and download the software update on behalf of its associated robotic surgical devices. Such a technique may reduce bandwidth requirements between a medical center and the surgical cloud service 310 as only one external download of the software update is required, while the robotic surgical devices 370-374 may retrieve the update using a medical center's local network from the communication hub 360. After obtaining the software update, the communication hub 360 may then transmit a message to one or more of its associated robotic surgical devices 370-374 to obtain the software update from it. Or in some examples, the surgical cloud service 310 may transmit the message to the communication hub 360 with a command to obtain the software update. The command may include an identification of one or more robotic surgical devices 370-374 to which the software update should be provided. In some examples, to avoid bandwidth saturation to the new software update, the management service 320 may determine an estimated time to download the new software package, and stagger software update messages to the managed device. For example, higher priority managed devices may be informed of the update before lesser priority devices.

At block 640, the surgical cloud service 310, e.g., via the management service 320, generates and transmits a message to one or more managed devices 360, 370-374 to install the obtained software update. In some examples, the surgical cloud service 310 may generate and transmit the message in response to receiving a message from one or more managed device 360, 370-374 indicating that the software package update has been successfully obtained; however, receipt of such a message is not required. For example, the message to install the obtained software update may be sent at the same time as the message described in block 630, or a single message with both indications or commands may be employed.

It should be appreciated that the message to install the obtained software update may be transmitted at any suitable time; it need not be transmitted immediately after the software update has been successful downloaded. For example, one or more medical centers may install the software package on one or a small subset of robotic surgical devices to test the update. After the test is successfully completed, the message to install the update may be transmitted to other robotic surgical devices that have already obtained a copy of the software update. Thus, the software update may be distributed to the robotic surgical systems, e.g., by storing it at one or more communication hubs or at the robotic surgical system(s) themselves. In some examples other conditions may be imposed on software updates. For example, an instruction may be provided to install a software update as soon as possible (or as soon as possible at or after a particular time), or at a specified date or time, or after a threshold period of idleness, etc. Thus, the instruction to install the software updates may include any suitable conditions.

At block 650, the surgical cloud service 310 receives a message from one or more managed devices 360, 370-374 indicating that the software package update was successfully installed. In some examples, the message may be sent immediately upon successful installation, while in other examples, the message may be sent at a later time, such as in response to a request for software version status from the surgical cloud service 310.

Figure 7:
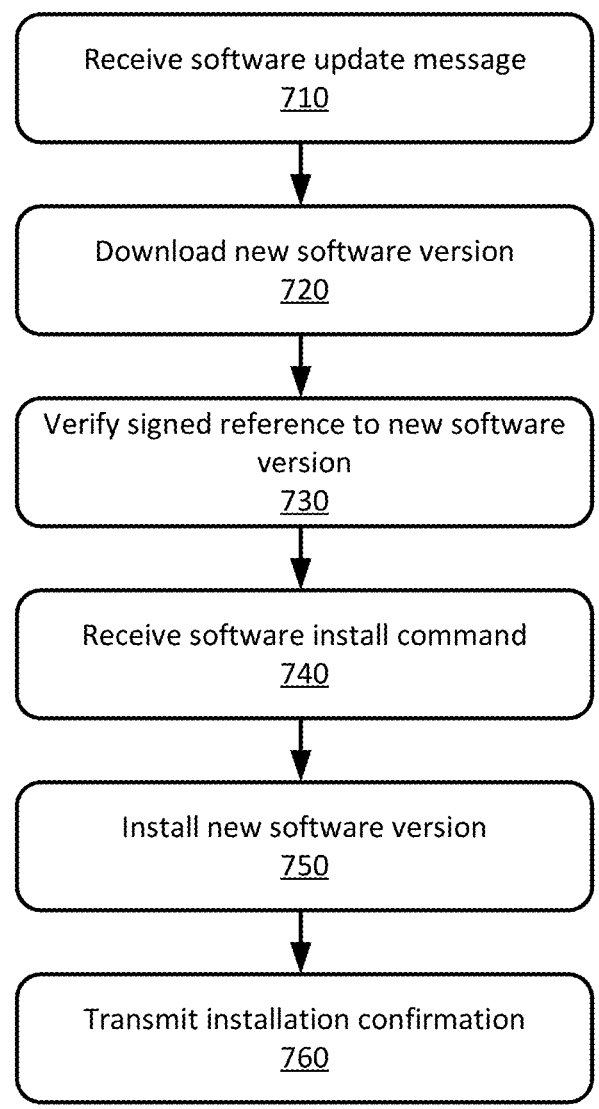

Referring now to FIG. 7, FIG. 7 shows an example method 700 for fleet management of robotic surgical systems. This example will be discussed with respect to the example system 300 shown in FIG. 3; however, any suitable system according to this disclosure may be employed, including those shown in FIGS. 1 and 2.

At block 710, a managed device 360, 370-374 receives a message indicating a new software package (or multiple software packages) is available for download. In this example, the managed device 360, 370-374 receives the message from the surgical cloud service 310; however, in some examples, the managed device 360, 370-374 may receive the message from another managed device 360, 370-374, such as a communication hub 360 (or from a different communication hub). For example, if a medical center has multiple communication hubs, one may obtain software updates on behalf of the entire medical center, and transmit messages to other communication hubs indicating the new software package is available. Furthermore, the new software package may not be a software package intended for the recipient of the message, but instead may be intended for another managed device. For example, a communication hub 360 may receive a message indicating a new software package for one or more robotic surgical systems is available. Furthermore, in some examples, a communication hub may intercept a message intended for a robotic surgical system and may obtain the software package on behalf of the intended recipient as discussed in more detail below.

At block 720, the recipient of the message obtains the identified software package(s). For example, the message may include a URL for the new software package, and the recipient of the message may download the software package from the URL.

At block 730, the recipient of the message may verify the downloaded software package(s). For example, if the URL includes a file containing a check value for the software package, the recipient of the message may also obtain the check value file and validate the downloaded software package using the check value(s) stored in the check value file. In some examples, the recipient of the message may also verify the software package by decrypting a signed reference to the software package. For example, as discussed above with respect to block 620 of FIGS. 6, the surgical cloud service 310 may create a signed reference to the software package, such as by encrypting a check value of the software package using its private key. Thus, the recipient of the message may decrypt the signed reference and use the decrypted check value to verify the software package.

At block 740, the managed device 360, 370-374 receives a software install command. As discussed above with respect to block 640 of FIG. 6, a software install command may be provided with the message indicating the new software package, or may be transmitted at a later time. Thus, the managed device 360, 370-374 may not install the new software package until it receives the software install command.

At block 750, in response to receiving the software install command, the managed device 360, 370-374 installs the new software package.

At block 760, after installing the new software package, the managed device 360, 370-374 may transmit a message to the surgical cloud service 310 (or the communication hub 360) indicating that the software was successfully installed.

Figure 8:
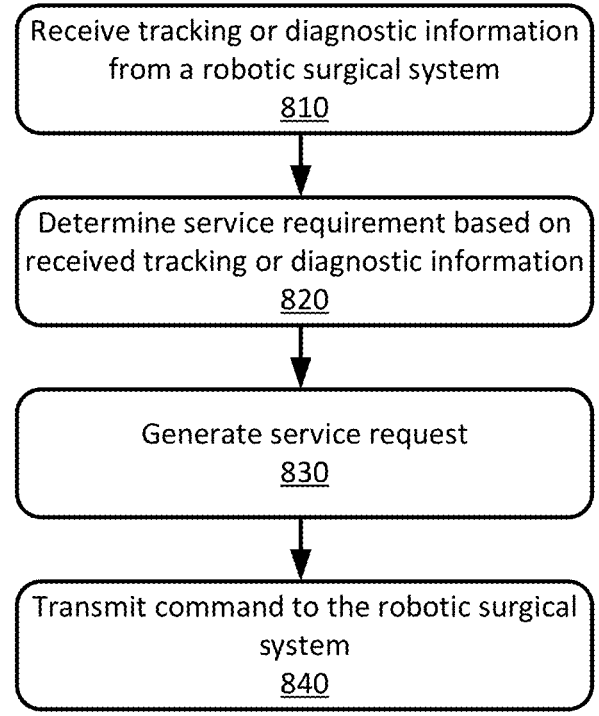

Referring now to FIG. 8, FIG. 8 shows an example method 800 for fleet management of robotic surgical systems. This example will be discussed with respect to the example system 300 shown in FIG. 3; however, any suitable system according to this disclosure may be employed, including those shown in FIGS. 1 and 2.

At block 810, the surgical cloud service 310 receives tracking or diagnostic information from a robotic surgical system 370-374. For example, the robotic surgical system 370-374 may transmit a period status message, e.g., a heartbeat message, indicating information about one or more subsystems or components of the robotic surgical system 370-374. Such subsystems or components may include input devices, actuators, sensors, surgical tools, software status (e.g., a list of executing processes or terminated processes), temperature, power consumption etc. The message may include usage information, e.g., a number of surgical procedures performed, a number of hours of usage, a number of uses of a particular surgical tool, etc. In some examples the tracking or diagnostic information may be sent in response to detecting an error, a failure, or a fault. For example, an error may occur if a software process halts. A fault or failure may occur if a hardware component fails or has reached an end of life condition, e.g., a maximum number of uses. Still other types of tracking or diagnostic information may be transmitted according to different examples.

At block 820, the surgical cloud service 310 determines a service requirement based on received tracking or diagnostic information. In this example, the surgical cloud service 310 determines trends or potential failures based on accumulated tracking or diagnostic information. For example, the operational temperature of an actuator during surgical procedures may be increasing over successive surgical procedures, indicating the actuator may be wearing out. Such trends may be detected using one or more trained machine learning models. For example, the surgical cloud service 310 may be provided with one or more such trained machine learning models to be used to detect such trends. In some examples, however, the surgical cloud service 310 may determine a service requirement based on a received error, failure, or fault condition, or it may determine that a surgical tool or other component has been used a threshold number of times. Further, an error, failure, or fault may be detected if a surgical tool connected to the robotic surgical system is determined to have lost regulatory approval or is subject to a recall. In some examples, the surgical cloud service 310 may determine a service requirement based on a duration since the last regular service of the robotic surgical system.

In some examples, a service requirement may be determined based on other operational states of the managed device, such as data storage usage has reached a threshold level, insufficient online time for data transfers, tampering with the managed device was detected, a user-initiated trouble report or service request, a threshold number of recoverable faults, failures, or errors have occurred within a threshold time period (e.g., within 2 hours), or a user-forced reboot of the managed device. Such events may indicate that a fault or failure is present or imminent in the device, or its normal operation is being interrupted due to user error or other misuse.

At block 830, the surgical cloud service 310 generates a service request. For example, the surgical cloud service 310 may generate a service request for regular maintenance and transmit the request to the provider of the robotic surgical system 370-374, or to the medical center itself, which can then schedule a representative to service the identified robotic surgical system 370-374. Alternatively (or in addition), a message to order a replacement part may be generated and transmitted to the medical center, or may be transmitted directly to a third party, such as a supplier or manufacturer of the robotic surgical system. Such messaging may be transmitted using one or more communication channels, such as a message transmitted to the robotic surgical system, to a pager or mobile device, to a text messaging application, etc. In some examples, an emergency service request may be generated if a major error, failure, or fault occurs, or if an error, failure, or fault occurs during a surgical procedure.

At block 840, the surgical cloud service 310 may generate and transmit one or more messages to the robotic surgical system 370-374. For example, if a major error, failure, or fault is detected, the surgical cloud service 310 may generate and transmit a shutdown command to the robotic surgical system. In some examples, the message may not be a shutdown message, but may instead be a message to be displayed on one or more of the robotic surgical system's display screens to notify a user of the system of the error, failure, or fault. Or the message may be a command to upload all available tracking or diagnostic information for one or more identified components, which may enable the surgical cloud service 310 to obtain more detailed information usable to identify a trend, or to identify a false positive of a possible error, failure, or fault.

Figure 9:
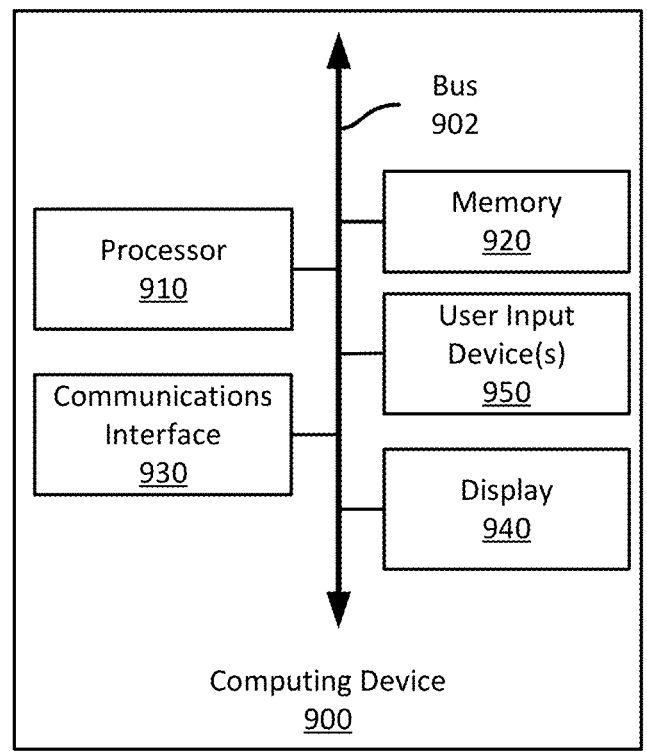
FIG. 9 shows an example computing device for fleet management of robotic surgical systems.

Referring now to FIG. 9, FIG. 9 shows an example computing device 900 suitable for use in example systems or methods for fleet management of robotic surgical systems according to this disclosure. The example computing device 900 includes a processor 910 which is in communication with the memory 920 and other components of the computing device 900 using one or more communications buses 902. The processor 910 is configured to execute processor-executable instructions stored in the memory 920 to perform one or more methods for fleet management of robotic surgical systems according to different examples, such as part or all of the example methods 400, or 600-800 described above with respect to FIGS. 4 and 6-8, respectively. The computing device, in this example, also includes one or more user input devices 950, such as a keyboard, mouse, touchscreen, microphone, etc., to accept user input. The computing device 900 also includes a 940 display to provide visual output to a user.

The computing device 900 also includes a communications interface 940. In some examples, the communications interface 930 may enable communications using one or more networks, including a local area network ("LAN"); wide area network ("WAN"), such as the Internet; metropolitan area network ("MAN"); point-to-point or peer-to-peer connection; etc. Communication with other devices may be accomplished using any suitable networking protocol. For example, one suitable networking protocol may include the Internet Protocol ("IP"), Transmission Control Protocol ("TCP"), User Datagram Protocol ("UDP"), or combinations thereof, such as TCP/IP or UDP/IP.

While some examples of methods and systems herein are described in terms of software executing on various machines, the methods and systems may also be implemented as specifically configured hardware, such as field-programmable gate arrays (FPGAs), specifically to execute the various methods. For example, examples can be implemented in digital electronic circuitry, or in computer hardware, firmware, software, or in a combination thereof. In one example, a device may include a processor or processors. The processor comprises a computer-readable medium, such as a random access memory (RAM) coupled to the processor. The processor executes computer-executable program instructions stored in memory, such as executing one or more computer programs. Such processors may comprise a microprocessor, a digital signal processor (DSP), an application-specific integrated circuit (ASIC), field programmable gate arrays (FPGAs), and state machines. Such processors may further comprise programmable electronic devices such as PLCs, programmable interrupt controllers (PICs), programmable logic devices (PLDs), programmable read-only memories (PROMs), electronically programmable read-only memories (EPROMs or EEPROMs), or other similar devices.

Such processors may comprise, or may be in communication with, media, for example computer-readable storage media, that may store instructions that, when executed by the processor, can cause the processor to perform the steps described herein as carried out, or assisted, by a processor. Examples of computer-readable media may include, but are not limited to, an electronic, optical, magnetic, or other storage device capable of providing a processor, such as the processor in a web server, with computer-readable instructions. Other examples of media comprise, but are not limited to, a floppy disk, CD-ROM, magnetic disk, memory chip, ROM, RAM, ASIC, configured processor, all optical media, all magnetic tape or other magnetic media, or any other medium from which a computer processor can read. The processor, and the processing, described may be in one or more structures, and may be dispersed through one or more structures. The processor may comprise code for carrying out one or more of the methods (or parts of methods) described herein.

The foregoing description of some examples has been presented only for the purpose of illustration and description and is not intended to be exhaustive or to limit the disclosure to the precise forms disclosed. Numerous modifications and adaptations thereof will be apparent to those skilled in the art without departing from the spirit and scope of the disclosure.

Reference herein to an example or implementation means that a particular feature, structure, operation, or other characteristic described in connection with the example may be included in at least one implementation of the disclosure. The disclosure is not restricted to the particular examples or implementations described as such. The appearance of the phrases "in one example," "in an example," "in one implementation," or "in an implementation," or variations of the same in various places in the specification does not necessarily refer to the same example or implementation. Any particular feature, structure, operation, or other characteristics described in this specification in relation to one example or implementation may be combined with other features, structures, operations, or other characteristics described in respect of any other example or implementation.

Use herein of the word "or" is intended to cover inclusive and exclusive OR conditions. In other words, A or B or C includes any or all of the following alternative combinations as appropriate for a particular usage: A alone; B alone; C alone; A and B only; A and C only; B and C only; and A and B and C.

That which is claimed is:
1. A method comprising:
 receiving, by a management server from a robotic surgical system, a provisioning request;
 in response to receiving the provisioning request:
  generating an encryption key pair for the robotic surgical system, the encryption key pair comprising a private key and a public key,
  communicating the private key to the robotic surgical system, and
  communicating a set of secure certificates to the robotic surgical system, at least one of the secure certificates enabling secure communications between the robotic surgical system and the management server;

receiving from the robotic surgical system, and using the at least one secure certificate enabling secure communications, a message indicating one or more software packages, each software package indicating a version of an installed software package on the robotic surgical system;

communicating one or more software updates to the robotic surgical system based on the message; and registering, at the management server, the robotic surgical system.

2. The method of claim 1, further comprising activating the robotic surgical system.

3. The method of claim 1, wherein the management server and the robotic surgical system are in communication via a robotic surgical hub device.

4. The method of claim 3, wherein the provisioning request comprises an identifier of the robotic surgical hub device, and further comprising:

associating, by the management server, the robotic surgical system and the robotic surgical hub device.

5. The method of claim 1, further comprising:

receiving an indication of a new software version;

generating a signed reference to the new software version;

providing the signed reference to the robotic surgical system;

receiving from the robotic surgical system a confirmation of installation of the new software version.

6. The method of claim 5, wherein the signed reference comprises a signed uniform resource locator ("URL").

7. The method of claim 1, wherein the robotic surgical system and the management server are located at a medical center.

8. The method of claim 1, wherein the robotic surgical system is located at a medical center, and the management server is located remotely from the medical center.

9. A system comprising:

one or more cloud management servers; and a plurality of robotic surgical systems remote from the cloud management server, each robotic surgical system in communication with the cloud management server and associated with a respective medical center, wherein the cloud management server is configured to:

receive, from a robotic surgical system located at a medical center, a provisioning request;

in response to receipt of the provisioning request:

generate an encryption key pair for the robotic surgical system, the encryption key pair comprising a private key and a public key, communicate the private key to the robotic surgical system, and communicate a set of secure certificates to the robotic surgical system, at least one of the secure certificates enabling secure communications between the robotic surgical system and the one or more cloud management servers;

receive from the robotic surgical system, and using the at least one secure certificate enabling secure communications, a message indicating one or more software packages, each software package indicating a version of an installed software package on the robotic surgical system;

communicate one or more software updates to the robotic surgical system based on the message; and register, at the management server, the robotic surgical system.

10. The system of claim 9, wherein the cloud management server comprises a web portal application, the web portal application providing functionality to provision, deprovision, and update software on each robotic surgical system of the plurality of robotic surgical systems.

11. The system of claim 10, wherein the web portal application is further configured to receive remote monitoring information from each robotic surgical system and schedule service based on the received remote monitoring information.

12. The system of claim 10, further comprising at least one robotic surgical hub device, the robotic surgical hub device located at a first medical center, the robotic surgical hub device associated with at least one of the robotic surgical systems associated with the first medical center, wherein the robotic surgical hub device is in communication with at least one robotic surgical system and the one or more cloud management servers, the robotic surgical hub device comprising at least one certificate associated with the one or more cloud management servers.

13. The system of claim 9, wherein the one or more cloud management servers are further configured to:

receive tracking or diagnostic information from a robotic surgical system;

determine a service requirement based on the received tracking or diagnostic information;

generate a service request based on the service requirement; and transmit a message to the robotic surgical system.

14. The system of claim 13, wherein determining a service requirement comprises determining a trend based on the received tracking or diagnostic information.

15. The system of claim 14, wherein determining the trend is based on a trained machine learning model.

16. The system of claim 13, wherein the message comprises an emergency shutdown message or a network disconnect command.

17. The system of claim 9, wherein the message revokes one or more certificates.

18. A non-transitory computer-readable medium comprising processor-executable instructions to cause a processor to:

receive, from a robotic surgical system, a provisioning request;

in response to receipt of the provisioning request:

generate an encryption key pair for the robotic surgical system, the encryption key pair comprising a private key and a public key, communicate the private key to the robotic surgical system, and communicate a set of secure certificates to the robotic surgical system, at least one of the secure certificates enabling secure communications between the robotic surgical system and a management server;

receive from the robotic surgical system, and using the at least one secure certificate enabling secure communications, a message indicating one or more software packages, each software package indicating a version of an installed software package on the robotic surgical system;

communicate one or more software updates to the robotic surgical system based on the message; and register the robotic surgical system.

19. The non-transitory computer-readable medium of claim 18, further comprising processor-executable instructions to cause a processor to activate the robotic surgical system.

\* \* \* \* \*